United States Patent
Khowala et al.

(10) Patent No.: US 6,946,277 B2
(45) Date of Patent: Sep. 20, 2005

(54) **METHOD FOR ENHANCING CELLOBIASE ACTIVITY OF *TERMITOMYCES CLYPEATUS* USING A GLYCOSYLATION INHIBITOR**

(75) Inventors: Suman Khowala, Calcutta (IN); Sumana Mukherjee, Calcutta (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/773,365

(22) Filed: Jan. 31, 2001

(65) Prior Publication Data

US 2002/0148009 A1 Oct. 10, 2002

(51) Int. Cl.$^7$ .................................................. C12N 9/24
(52) U.S. Cl. ...................... 435/200; 435/171; 435/244; 435/155
(58) Field of Search ................................ 435/171, 155, 435/200, 244

(56) References Cited

PUBLICATIONS

Kubicek et al., Canadian Journal of Microbiology, vol. 33, pp. 698–703.*

Bhattacharyya et al., "Purification and characterization of an extracellular beta–xylosidase from *Termitomyces clypeatus*", Biotechnology Progross 13 (6): 822–825 (1997).*

Roy et al., "Development of high molar mass cellobiase comples by spontaeous protein–protein interaction in the culture filtrate of *Termitomyces clypeatus*", Folia Microbiologica 39 (6): 463–70 (1994).*

Sengupta et al., "Purification and Characterization of a beta glucosidase cellobiase from *Termitomyces clypeatus*", Biochim. Biophys. Acta 1076 (2): 215–20 (1991).*

* cited by examiner

*Primary Examiner*—Irene Marx
(74) *Attorney, Agent, or Firm*—Harness Dickey & Pierce, PLC

(57) ABSTRACT

This invention provides a method for enhancing the cellobiase activity of the strain *Termitimyces clypeatus* using 2-deoxy-D-glucose as glycosylation inhibitor, said process comprises inoculating and growing mycelial culture of (the edible mushroom) *Termitimyces clypeatus*, in sterilized medium containing 0.05 to 5.0% of 2-deoxy-D-glucose in addition to 0.5 to 2.0% of cellobiose, succinate—0.5%, 2 to 3% of ammonium di hydrogen phosphate and conventional micro-nutrients at pH between 3 to 8 and incubating at temperatures between 20–35° C. under shaking in aerobic conditions, and separating the culture medium by known methods, and using the culture filtrate directly as the source of the enzyme cellobiase and also for endo-glucanase and cellobiohydrolase for use in cellulose hydrolysis.

10 Claims, No Drawings

METHOD FOR ENHANCING CELLOBIASE ACTIVITY OF *TERMITOMYCES CLYPEATUS* USING A GLYCOSYLATION INHIBITOR

FIELD OF THE INVENTION

This present invention relates to a novel edible mushroom strain *Termitomyces clypeatus* and a method for enhancing cellobiase activity of the novel strain *Termitomyces clypeatus* using 2-deoxy-D-glucose as glycosylation inhibitor.

BACKGROUND AND PRIOR ART REFERENCES

An enzyme preparation containing high cellobiase activity is useful for enzymatic hydrolysis of cellulose, leading to production of glucose, which in turn may be converted to ethanol to be used as an alternative and renewable energy source. Cellulose comprises the most abundant source of fermentable carbohydrates in the world as plant biomass. When biologically converted to fuels, such as ethanol and various other low-value high volumes commodity products, this vast resource can provide environmental, economic and strategic benefits on a large scale unparalleled by any other sustainable resource as referred by—Handbook on Bioethanol Production and utilization. Applied Energy Technology Series, Washington, D.C. Taylor and Francis (1996); and Science (1991), volume 251, pages 1318–1323; and Annual Review of Energy and Environment (1996), volume 21, pages 403–465.

Reese E. T. and Mandels M. during 2nd World war detected cellulase enzyme activity in *Trichoderma viride*, when the fungus destroyed clothing and plants. Following the war they turned their efforts towards discerning the biochemical mechanisms of cellulase action to convert cellulosic biomass into glucose syrup. Reference may be made to Reese E. T. and Mandels M. (1971). Cellulose and cellulose derivatives (Eds. Bikales, N and Segal. L.) John Wiley & Sons, pages 1079–1094; wherein it was emphasized that cellulase is not a single enzyme but a group of enzymes e.g. endo-glucanase, cellobiohydrolase and cellobiase, which must act synergistically to achieve saccharification of cellulose. Reference may be made to Nisizawa K. (1973) Journal of Fermentation Technology, volume 51, pages 267–304; and Wood T. M. (1975) Biotechnology and Bioengineering Symposium, volume 5, pages 111–137, wherein it was proposed that an initial random attack on the cellulose molecule was achieved by the action of the endo-glucanase (Enzyme Commission number 3.2.1.4) and followed immediately by the action of the cellobiohydrolase (Enzyme Commission Number 3.2.1.91), which released the disaccharide cellobiose, from the non-reducing end of the cellulose. Continued synergism between the two enzymes resulted in solubilization of the cellulose into sugar syrups containing small oligosaccharides and cellobiose. The activity of third enzyme, cellobiase (Enzyme Commission Number 3.2.1.21) is required if glucose syrups are envisaged as the product. Cellobiase converts the oligosaccharides of glucose with degree of polymerization 2 to 7 ($G_2$–$G_7$) into glucose.

There is a great deal of interest in developing methods to produce glucose syrups from cellulose using cellulase preparations. It is generally agreed that cheap glucose is the key intermediate for subsequent chemical and energy products. Activity of endo-glucanase and cellobiohydrolase of cellulolytic enzymes are inhibited by cellobiose. This inhibition is relieved by hydrolysis of cellobiose to glucose by cellobiase. Hence, cellobiase plays an important role in maximizing cellulose hydrolysis. Reference may be made to Archer B. D. and Peberdy J. F. (1997) Current Reviews in Biotechnology, volume 17(41), pages 273–306, wherein it has been stated that action of cellobiase on cellulose is the rate determining step of the entire cellulose hydrolysis, as cellobiase reduces the inhibition of cellulase activity by cellulose derived cellobiose and cellobiase is the key enzyme of cellulose hydrolysis. Reference may also be made to Reczy K., Brumbauer A., Book M., Szengyl Z. S. and Zacchi G. (1998) Applied Biochemistry and Biotechnology, volume 225, pages 70–72, wherein it has been stated that hydrolysis of cellulose by cellulases often results in a mixture of glucose, cellobiose and low molecular weight cellodextrins, and that cellobiose is nonfermentable for most yeasts, and therefore it has to be hydrolyzed to glucose by cellobiase (or β-glucosidase) prior to ethanol fermentation. Reference may be made to Kadam S. K. and Demain A. L. in Biochemical and Biophysical Research Communication (1989) volume 161, pages 706–711, which states that addition of cloned β-glucosidase enhances the degradation of crystalline cellulose by the *Clostridium thermocellum* cellulose complex.

The cellobiase activity secreted by *Trichoderma*/*Aspergillus* and its mutants was sub-optimal for conversion of cellulose to glucose. Efforts have been made to enhance the cellulolytic activity of *Trichoderma*/*Neurospora*/*Aspergillus* by media manipulations, by genetic engineering and by mutagenesis. Reference may be made to Abdel-Fattah A. F., Osman M. Y., Abdel-Naby M. A. Chemical Engineering Journal (1997) volume 68, pages 189–196, wherein a strain of *Aspergillus niger* A-20 was engineered for cellobiase production and so far the highest activity of cellobiase produced is 27.5 u/ml. Reference may be made to Strauss J. and Kubicek C. P. in Journal of General Microbiology (1991) volume 136, pages 1321–1326, where a mutant strain of fungus *Trichoderma reesei* M8, obtained by γ-irradiation of *Trichoderma reesei* QM9414, is said to produce 23 u/ml of cellobiase.

Similarly, efforts have been made to increase the production and secretion of cellobiase activity. Reference may be made to Sternberg D. and Mandels G. R. (1979) Journal of Bacteriology, volume 139, pages 761–769, wherein Sophorose was used for induction of cellulase and cellobiase in *Trichoderma reesei*. But cellobiase activity remained in the mycelium of the fungus. Reference may be made to Yazdi M. T., Woodward J. R. and Radford A. (1990), Journal of general Microbiology, Volume 136, pages 1313–1319, where effect of addition of some surfactants and amino acids were found to have adverse effect on production of cellobiase in *Neurospora crassa*.

Reference may be made to Kubicek C. P., Panda T., Schreferl- Kunar G., Gruber F- and Messner R. (1987), Canadian Journal of Microbiology, Volume 33, pages 698–703, wherein production and secretion of cellobiase in *Trichoderma reesei* was studied in presence of glycosylation inhibitors Tunicamycin and 2-deoxy-D-glucose. Tunicamycin (0–50 μg/ml) had no effect on secretion of proteins in the fungus and 2-deoxy-D-glucose inhibited the biosynthesis of extracellular as well as intracellular protein over a wide range of concentration (0–150 μg/ml).

The drawback in hydrolysis of cellulose is that by using other methods for production of enhanced cellobiase activity, such as by media manipulations or by genetic engineering or by mutagenesis of the strains used for enzyme production, yield of cellobiase upto the maximum level of 27.5 u/ml could be obtained (in the culture medium of *Aspergillus niger* A-20 by Abdel-Fattah A. F., Osman M. Y., Abdel-Naby M. A. Chemical Engineering Journal (1997) volume 68, pages 189–196). Cellulolytic enzymes are generally reported to be glycoproteins and glycosylation is known to effect activation or retardation of protein synthesis, protein trafficking and secretion as well as in catalytic function and enzyme stability for extracellular proteins and enzymes. Use of glycosylation inhibitors in the growth medium of *Trichoderma reesei* however did not improve the production of enzyme, but affected secretion only.

OBJECTS OF THE INVENTION

The main object of the present invention relates to a novel edible mushroom strain *Termitomyces clypeatus* and a method for enhancing cellobiase activity of the novel strain *Termitomyces clypeatus* using 2-deoxy-D-glucose as glycosylation inhibitor Another object of the present invention is to provide a process for the preparation of an enzyme composition containing enhanced cellobiase activity useful for the hydrolysis of cellulose, by fermentation of a mycelial culture of an edible mushroom *Termitomyces clypeatus*.

Still another object of the invention is the use of said enzyme composition for hydrolysis of crystalline and amorphous cellulose to glucose.

Yet, objective of the present invention is to provide an enzyme preparation that contains endo-glucanase activity, in addition to cellobiase, which will help in better hydrolysis of cellulose.

Yet, another objective of the present invention is to provide an enzyme preparation that contains cellobiohydrolase activity, in addition to cellobiase and endo-glucanase, which will help in still better hydrolysis of cellulose.

Yet, another objective of the present invention provides no additional step requirement for the action of enzyme preparation for cellulose hydrolysis.

Yet, another objective of the present invention is to provide all these enzymes in single fermentation of the edible mushroom.

SUMMARY OF THE INVENTION

Accordingly to meet the above objects, this invention provides a method for enhancing the cellobiase activity of the strain *Termitomyces clypeatus* using 2-deoxy-D-glucose as glycosylation inhibitor, said process comprises inoculating and growing mycelial culture of (the edible mushroom) *Termitomyces clypeatus*, (Ghosh A. K. and Sengupta S., Journal of Food Sciences And Technology; vol 15. No.6, pp 237–242, 1978; and ibid Vol 19, pp 57–60, 1982) in sterilized medium containing 0.05 to 5.0% of 2-deoxy-D-glucose in addition to 0.5 to 2.0% of cellobiose, succinate—0.5%, 2 to 3% of ammonium di hydrogen phosphate and conventional micro-nutrients at pH between 3 to 8 and incubating at temperatures between 20–35° C. under shaking in aerobic conditions, and separating the culture medium by known methods, and using the culture filtrate directly as the source of the enzyme cellobiase and also for endo-glucanase and cellobiohydrolase for use in cellulose hydrolysis.

DETAILED DESCRIPTION OF THE INVENTION

Accordingly, the present invention provides a method for enhancing the cellobiase activity of the strain *Termitomyces clypeatus* using 2-deoxy-D-glucose as glycosylation inhibitor which comprises inoculating and growing mycelial culture of the edible mushroom, *Termitomyces clypeatus*, (having the accession number IICB-411, given by Indian Institute of Chemical Biology, Calcutta, India, a constituent laboratory of the applicants), in sterilized medium containing 2-deoxy-D-glucose, cellobiose, ammonium di hydrogen phosphate and conventional micronutrients at pH between 3–8 and incubating at temperatures between 20–35° C. under shaking in aerobic conditions and separating the culture filtrate by known methods, using the culture filtrate directly as the source of enzyme cellobiase, endo-glucanase and cellobiohydrolase for use in cellulose hydrolysis.

In an embodiment of the present invention, the mycelial culture of the edible mushroom *Termitomyces clypeatus* was characterized by different physical and biochemical properties.

Physical properties: The strain produces silky white colony on solid medium, frequently producing aggression of mycelia inn areas to form strands and knots of mycelia. The hyphae produced are tubular undifferentiated and hyphae of subcuits with short branch are also present. The average diameter of the hyphae is between 5 to 10 micrometer and all are septed. The strain under microscope shows absence of any sporophoric structure or any basidiospore. A few clamp connections characteristic of mushroom culture is also visible within the hyphae. Hyphae with both single and double nucleus are present. The culture remain white over a long period of growth, say 10 to 15 days without any coloration due to any sporulation. Biochemical properties: The mycelial culture is a brown-rot type and has no phenol oxidase or laccase activity. It grows well in defined medium containing carbohydrate and mineral salts. The growth is not well supported by glucose but highly stimulated by glucose polysaccharides. The strain has optimum C/N ratio at 5 and 10 for optimum growth in synthetic medium. Trace elements like $Fe^{++}$, $Mn^{++}$, $Zn^{++}$, $Ca^{++}$ and $Mo^{++}$ have much influence on growth. The dry mycelia obtained in liquid medium at optimum growth phase has composition as: protein 31.76%, carbohydrate 52.0%, fat 1.0%, fiber 10.5% and ash 2.7%. The strain in suitable medium gives positive tests for Carboxymethyl cellulase, Cellobiase. Invertase, Amylglucosidase, amylase, endo-xylanse, arabinofuranosidase, acety esterase and xylosidase activities but negative tests for laccase, phenol oxidase, chitinase and mannanase.

In another embodiment of the present invention, the mycelial culture of the edible mushroom *Termitomyces clypeatus* having accession number IICB-411, given by Indian Institute of Chemical Biology, Calcutta, a constituent laboratory of Council of Scientific and Industrial Research, India is used.

The organism used is fungus *Termitiomyces clypeatus* II CB-411 strain having Accession No. MTCC 591, deposited on Oct. 24, 2001 at Institute of Microbial Technology (IMTECH), Chandigarh, India, Sector 39 A, Chandigarh 160 036, India, under the terms of the Budapest Treaty. This strain is open to public access and can be acquired/obtained from IMTECH, Chandigarh. The strain has been deposited with the Microbial Type Culture Collection & Gene Bank, Institute of Microbial Technology. The deposit will be maintained in the depository, which is public depository, for a period of 30 years, or 5 years after the most recent request, or for the effective life of a patent, whichever is longer, and will be replaced if the deposit becomes depleted or non-viable during that period. Samples of the deposit will become available to the public and all restrictions imposed on access to the deposit will be irrevocably removed upon grant of a patent on this application.

In another embodiment of the present invention, the strain is cultivated on a medium containing an assimilable carbon and nitrogen sources, TCA cycle or amino acids, inorganic salts and organic nutrients, in presence of glycosylation inhibitors.

In yet another embodiment, the assimilable carbon sources are carbohydrates selected for the preparation consisting of cellobiose, mannose, fructose, xylose, arabinose, starch, dextrin, cellulose, cotton, xylan and agrowastes like baggasse powder, rice-straw powder, wheat bran, corn cob powder, corn powder in presence of TCA cycle acids like succinate, fumarate, maleate or amino acids like aspartate, glutamate, serine, histidine and alanine or glucose analogue like D-glucosamine.

In yet another embodiment, glycosylation inhibitors used are Tunicamycin, deoxy nojirimycin, 2-deoxy glucose and D-glucono-lactone.

In yet another embodiment, assimilable nitrogen sources used may be ammonium chloride, ammonium nitrate, ammonium di hydrogen phosphate, and potassium nitrate.

In yet another embodiment organic nutrients used may be malt extract, yeast extract and potato extract, peptone, soya-peptone, bactopeptone, corn steep liquor.

In yet another embodiment, detergents used were Tween-20, Tween-80, and Tween-100.

The fungus is maintained in agar slants containing (w/w) glucose 5%, potato extract 10%, malt extract 5%, $KH_2PO_4$ 0.087%, $MgSO_4$, $7H_2O$ 0.05%. Cultivation of the fungus is carried out between temperatures 20–37° C., preferably at 28–30° C. and at pH between 3–8, preferably at 4–6, under aerobic condition in shake flask in liquid medium on a rotary shaker (200–300 strokes per minute). Among the assimilable carbon sources (cellobiose, mannose, fructose, xylose, arabinose, starch, dextrin, cellulose, cotton, xylan and agro-wastes like baggasse powder, rice-straw powder, wheat bran, corn cob powder, corn powder; in presence of TCA cycle acids like succinate, fumarate, maleate or amino acids like aspartate, glutamate, serine, histidine and alanine or glucose analogues like D-glucosamine) D-cellobiose with succinate served as one of the best carbon sources in the concentration range of 0.5–2%(w/v). Among the assimilable nitrogen sources (ammonium chloride, ammonium nitrate, ammonium di hydrogen phosphate, potassium nitrate and organic nitrogen sources such as malt extract, yeast extract, potato extract, soya-peptone and bactopeptone) ammonium di hydrogen phosphate was used. Among the glycosylation inhibitors (Tunicamycin, deoxynojirimycin, 2-deoxy-D-glucose and D-glucono-lactone) 2-deoxy glucose was preferred (Table 1). Detergents used were Tween 20, Tween-80, or Tween-100. Initial pH of the medium may be maintained at 3–7, preferably at 4.5. Inoculum is prepared in the medium in polypropylene conical flask with sterile glass balls (1–1.5 cm in diameter) 3–4 numbers in 250-ml flask. The fine mycelia grown in liquid medium after 2–4 days of growth were added to the fermentation medium at the ratio of 1:10 (v/v). Optimum production of enzyme took place after 3 days of inoculation, between 4–6$^{th}$ days. The culture filtrate is freed from mycelia by any known method of filtration. Cellobiase activity of the culture medium was assayed using p-nitro phenyl β-D-glucoside as substrate. Reference may be made to Khowala. S. And Sengupta. S. (1992) Enzyme and microbial Technology, volume 14, pages144–149. One unit of activity was taken as the amount of enzyme, which could liberate one micromole of p-nitro phenol from p-nitro phenyl β-D-glucoside in the reaction mixture incubated at 50° C. for 30 minutes (Table 1 and 2).

Endo-glucanase and cellobiohydrolase activities were measured by dinitrosalicylic acid reagent using carboxy methylcellulose (Sigma chemical co.) and crystalline cellulose (Sigma chemical co.) respectively as substrate (Table 2). Reference may be made to Sumner J. B. and Sumner G. (1949) in Laboratory Experiments in Chemistry, Academic press, New York, page 38. One unit of enzyme was considered as the amount of enzyme that could liberate one micromole of glucose equivalent per minute in buffer at pH 5.0 at 50° C.

Novelty of the method lies in production of high cellobiase activity, in presence of 2-deoxy-D-glucose by *Termitomyces clypeatus*, without.any genetic manipulation of the organism, not hitherto reported from any other organism.

The inventive step is the addition of 2-deoxy-D-glucose in the growth medium in presence of assimilable carbon and nitrogen sources and other nutrients. 2-deoxy-D-glucose is non-fermentable analogue of glucose and mannose, and is known to interfere in formation of wall polysaccharides in yeast [Reference may be made to European Journal of Biochemistry (1975), Volume 54, pages 459–467] and to increase protein secretion in *Trichoderma reesei* [Reference may be made to Journal of General Microbiology (1989) Volume 135, pages 301–307]; but it acts as a glycosylation inhibitor, increases synthesis and secretion of extracellular proteins in *Termitomyces clypeatus*, when used in the concentration range of 0.05 to 5%(w/v) and high cellobiase activity is produced in presence of cellobiose, as determined in the applicants laboratory. At higher concentrations, 2-deoxy-D-glucose inhibit growth of the fungus *T. clypeatus* and at lower concentrations, the effect is not observed on enhanced production and secretion of enzyme (Table1), but growth is similar to that in control medium.

TABLE 1

Cellobiase activity in presence of glycosylation inhibitors

| Samples | Cellobiase activity (units/ml) |
|---|---|
| Control | 1.044 |
| Control + Tunicamycin (10 μg/ml) | 1.2075 |
| Control + 1-deoxynojirimycin (80 μM) | 1.4085 |
| Control + 2-deoxy-D-glucose (0.05 mg/ml) | 2.236 |
| Control + 2-deoxy-D-glucose (1 mg/ml) | 50.097 |
| Control + 2-deoxy-D-glucose (5 mg/ml) | 0.081 |
| Control + glucono-lactone (2 mg/ml) | 6.1820 |

TABLE 2

Cellulolytic activities produced in *Termitomyces clypeatus*

| Sample | Cellobiase activity (units/ml) | Endo-glucanase activity (units/ml) | Cellobio-hydrolase activity (units/ml) |
|---|---|---|---|
| Cellobiose (10 mg/ml) + succinate (5 mg/ml) + ammonium di hydrogen phosphate (24 mg/ml) [Control medium] | 1.443 | 1.085 | 1.909 |
| Control medium + 2-deoxyglucose (1 mg/ml) (Example 1) | 50.097 | 4.112 | 3.546 |
| Control medium + 2-deoxy-D-glucose (300 μg/ml) (Example 2) | 90.020 | 4.637 | 3.600 |
| Control medium + 2-deoxy-D-glucose (1 mg/ml) + Mannose (500 μg/ml) | 140.60 | 1.086 | 4.873 |

The following examples are given by the way of illustration of the present invention and should not be construed to limit the scope of the present invention.

EXAMPLE 1

The fungus *Termitomyces clypeatus* IICB-411 was grown in a medium containing (w/w, %): Cellobiose 1, 2-deoxy-D-glucose 0.30, sodium succinate 0.5, $KH_2PO_4$ 0.087, $MgSO_4$, $7H_2O$ 0.05 at pH 4.5. The 250 ml conical flask containing 50 ml of medium were autoclaved for 20 minutes at 15 pounds per square inch pressure, where separately autoclaved ammonium di hydrogen orthophosphate at the concentration of 2.4% w/w was added to the medium after sterilization. The medium was cooled and was inoculated at the rate of 10% mycelia (blended) of the fungus developed earlier in flasks with glass marbles. The culture was grown in the medium for 4 days at temperatures 28°–32° C. on a rotary-shaker. The culture filtrate was freed from mycelia and the clear supernatant was used as a source of enzymes. Cellobiase activity was 90 units per ml, endo-glucanase was 4.5 units per ml, and cellobiohydrolase was 3.5 units per ml, respectively. Cellobiase activity in absence of 2-deoxy-D-glucose in the control medium was 1.44 units per ml.

EXAMPLE 2

The fungus *Termitomyces clypeatus* IICB-411 was grown in a medium containing (w/w, %): Cellobiose 1, 2-deoxy-D-glucose 0.5, mannose 0.5, sodium succinate 0.5, $KH_2PO_4$ 0.087, $MgSO_4$, $7H_2O$ 0.05 at pH 4.5. The 250 ml conical flask containing 50 ml of medium were autoclaved for 20 minutes at 15 PSI pressure, where ammonium di hydrogen orthophosphate at the concentration of 2.4% w/w was autoclaved separately at same conditions and was added to the medium only after sterilization. The medium was cooled and was inoculated at the rate of 10% mycelia (blended) of the fungus developed earlier in flasks with glass marbles. The culture was grown in the medium for 4 days at temperatures 28°14 32° C. on a rotary-shaker. The culture filtrate was freed from mycelia and the clear supernatant was used as a source of enzymes. Cellobiase activity was 140 units per ml and endo-glucanase was 6 units per ml and cellobiohydrolase was 3.5 units per ml, respectively. Cellobiase activity in absence of 2-deoxy-D-glucose in the control medium with mannose was 1.345 units per ml.

EXAMPLE 3

The fungus *Termitomyces clypeatus* IICB-411 was grown in a medium containing (w/w, %): Cellobiose 1, 2-deoxy-D-glucose 1, sodium succinate 0.5, $KH_2PO_4$ 0.087, $MgSO_4$, $7H_2O$ 0.05 at pH 4.5. The 250 ml conical flask containing 50 ml of medium were autoclaved for 20 minutes at 15 psi pressure, where ammonium di hydrogen orthophosphate at the concentration of 2.4% w/w was autoclaved separately at same conditions and was added to the medium only after sterilization. The medium was cooled and was inoculated at the rate of 10% mycelia (blended) of the fungus developed earlier in flasks with glass marbles. The culture was grown in the medium for 4 days at temperatures 28°–32° C. on a rotary-shaker. The culture filtrate was freed from mycelia and the clear supernatant was used as a source of enzymes. Cellobiase activity was 50 units per ml, endo-glucanase was 4 units per ml, and cellobiohydrolase was 3.5 units per ml, respectively. Cellobiase activity in absence of 2-deoxy-D-glucose in the control medium was 1.44 units per ml.

TABLE 3

Maximum cellobiase activity

| Organism | Cellobiase (U/ml) |
|---|---|
| *Aspergillus niger*[A] (Genetically engineered strain) | 27.5[A] |
| *Trichoderma reesei*[B] (mutagenised strain) | 23.0[B] |
| *Termitomyces clypeatus* (in presence of 2-deoxyglucose) | 90.0 (Example-1) |
| *Termitomyces clypeatus* (in presence of 2-deoxyglucose) | 140.0 (Example-2) |
| *Termitomyces clypeatus* (in presence of 2-deoxyglucose) | 50.0 (Example-3) |
| *Termitomyces clypeatus* (in absence of 2-deoxyglucose) | 1.44 |
| *Dichomitus squalenes*[C] (in presence of 2-deoxyglucose) | 0.05[C] |

[A]Reference from Abdel-Fattah A. F., Osman M. Y., Abdel-Naby M. A. in Chemical Engineering Journal (1997) volume 68, pages 189–196.
[B]Reference from Strauss J. and Kubicek C. P. in Journal of General Microbiology (1991) volume 136, pages 1321–1326.
[C]Activity was measured in the laboratory with *Dichomitus squalenes* in a similar medium as that used for *Termitomyces clypeatus*.

The Main Advantages of the Present Invention are:
i) The enzyme preparation contains highest cellobiase activity in units per ml produced, so far reported from any other known organisms.
ii) Simply modulating media composition and fermentative conditions, without any genetic manipulation of the organism produces the activity.
iii) The enzyme preparation contains other cellulolytic activities, like endo-glucanase and cellobiohydrolase activities useful for better hydrolysis of cellulose, which are obtained in a single fermentation.
iv) The enzyme preparation is obtained from an edible mushroom, which is being consumed by people for a long time beyond record and the species is recorded as edible mushroom in literature. So, the enzyme preparation can be used directly for human consumption purposes, such as in processing of food products and medical aids etc. without any risk.
v) The potency of the enzyme preparation can be easily determined by the assay of enzyme activities according to the methods that can be performed easily.
vi) The enzyme activities are stable at room temperature (below 30° c.) and do not promote microbial growth under the prescribed condition.
vii) The culture filtrate after completion of growth can be directly used after filtration as source of enzyme.
viii) It uses the most abundant source of fermentable carbohydrates in the world as plant biomass.

What is claimed is:
1. A method for producing cellobiase, said method comprising the steps of:
  (a) inoculating a mycelial culture of the *Termitomyces clypeatus* II CB-411 into sterilized medium containing carbon and nitrogen sources, inorganic salts, organic nutrients and glycosylation inhibitor 2-deoxy-D-glucose in the range of 0.05 mg/ml to 2 mg/ml at a pH of between 3 to 8;
  (b) growing the mycelial culture at temperatures between 20–37° C. under shaking aerobic conditions; and
  (c) separating culture medium from the mycelia to obtain cellobiase activity in the range of 2.236 units/ml to 140.60 units/ml.

2. The method of claim 1, wherein the carbon source is selected from the group consisting of carbohydrates, agrowastes, TCA cycle acids, amino acids, and D-glucosamine, wherein the carbohydrates are selected from the group consisting of cellobiose, mannose, fructose, xylose, arabinose, starch, dextrin, cellulose, cotton, and xylan; wherein agrowastes are selected from the group consisting of baggasse powder, rice-straw powder, wheat bran, corn cob powder, and corn powder; wherein the TCA cycle acids are selected from the group consisting of succinate, fumarate, and maleate; and wherein the amino acids are selected from the group consisting of aspartate, glutamate, serine, histidine, and alanine.

3. The method of claim 1, wherein the nitrogen source is selected from the group consisting of ammonium chloride, ammonium nitrate, ammonium dihydrogen orthophosphate, and potassium nitrate.

4. The method of claim 1, wherein the sterilized medium comprises an organic nutrient selected from the group consisting of malt extract, yeast extract, potato extract, peptone, soya-peptone, bactopeptone, and corn steep liquor.

5. The method of claim 1, wherein the sterilized medium further comprises a detergent selected from group consisting of Tween-20, Tween-80, and Tween-100.

6. The method of claim 1, wherein activity of cellobiase is about 2.23 units/ml and the 2-deoxy-D-glucose is present at a concentration of about 0.05 mg/ml.

7. The method of claim 1, wherein activity of cellobiase is about 50.09 units/ml and the 2-deoxy-D-glucose is present at a concentration of about 1 mg/ml.

8. The method of claim 1, wherein activity of cellobiase is about 90 units/ml and the 2-deoxy-D-glucose is present at a concentration of about 300 $\mu$g/ml.

9. The method of claim 1, wherein activity of cellobiase is about 140 units/ml, the 2-deoxy-D-glucose is present at a concentration of about 1 mg/ml and mannose is present at a concentration of about 500 $\mu$g/ml.

10. The method as claimed in claim 1, wherein the carbon source is selected from the group consisting of cellobiase mannose and succinate.

* * * * *

UNITED STATES PATENT AND TRADEMARK OFFICE
CERTIFICATE OF CORRECTION

| | | |
|---|---|---|
| PATENT NO. | : 6,946,277 B2 | |
| APPLICATION NO. | : 09/773365 | |
| DATED | : September 20, 2005 | |
| INVENTOR(S) | : Suman Khowala et al. | |

It is certified that error appears in the above-identified patent and that said Letters Patent is hereby corrected as shown below:

Column 4, line 11, start a new paragraph and insert --The organism used is fungus Termitiomyces clypeatus II CB-411 strain having Accession No. MTCC 591, deposited on October 24, 2001 at Institute of Microbial Technology (IMTECH), Chandigarh, India, Sector 39 A, Chandigarh 160 036, India, under the terms of the Budapest Treaty. This strain is open to public access and can be acquired/obtained from IMTECH, Chandigarh. The strain has been deposited with the Microbial Type Culture Collection & Gene Bank, Institute of Microbial Technology. The deposit will be maintained in the depository, which is public depository, for a period of 30 years, or 5 years after the most recent request, or for the effective life of a patent, whichever is longer, and will be replaced if the deposit becomes depleted or non-viable during that period. Samples of the deposit will become available to the public and all restrictions imposed on access to the deposit will be irrevocably removed upon grant of a patent on this application.--

Column 4, lines 51-67 delete the following "The organism used is fungus Termitiomyces clypeatus II CB-411 strain having Accession No. MTCC 591, deposited on October 24, 2001 at Institute of Microbial Technology (IMTECH), Chandigarh, India, Sector 39 A, Chandigarh 160 036, India, under the terms of the Budapest Treaty. This strain is open to public access and can be acquired/obtained from IMTECH, Chandigarh. The strain has been deposited with the Microbial Type Culture Collection & Gene Bank, Institute of Microbial Technology. The deposit will be maintained in the depository, which is public depository, for a period of 30 years, or 5 years after the most recent request, or for the effective life of a patent, whichever is longer, and will be replaced if the deposit becomes depleted or non-viable during that period. Samples of the deposit will become available to the public and all restrictions imposed on access to the deposit will be irrevocably removed upon grant of a patent on this application."

UNITED STATES PATENT AND TRADEMARK OFFICE
CERTIFICATE OF CORRECTION

PATENT NO. : 6,946,277 B2
APPLICATION NO. : 09/773365
DATED : September 20, 2005
INVENTOR(S) : Suman Khowala et al.

It is certified that error appears in the above-identified patent and that said Letters Patent is hereby corrected as shown below:

Column 7, line 39, delete "28°14 32°" and insert --28° - 32°--.
Column 10, line 18, delete "cellobiase" and insert --cellobiase,--.

Signed and Sealed this

Eighth Day of August, 2006

JON W. DUDAS
*Director of the United States Patent and Trademark Office*